United States Patent [19]

DeBan et al.

[11] Patent Number: 5,301,681
[45] Date of Patent: Apr. 12, 1994

[54] DEVICE FOR DETECTING CANCEROUS AND PRECANCEROUS CONDITIONS IN A BREAST

[76] Inventors: Abdou F. DeBan, 1431 Wilmington Ave. Apt. 309, Dayton, Ohio 45420; David M. Tumey, 8280 Millspring Pl., Dayton, Ohio 45424; Jonathon W. Reeves, 207 W. Center College, Yellow Springs, Ohio 45387; David B. McQuain, 964 Ashcreek Dr., Dayton, Ohio 45458; William H. Reeves, 10449 Steam Park Ct., Spring Valley, Ohio 45370; Carole C. Reeves, 10449 Steam Park Ct., Spring Valley, Ohio 45370; Elias D. Aboujaoude, 1430 Kylemore Dr., Xenia, Ohio 45385

[21] Appl. No.: 768,373

[22] Filed: Sep. 27, 1991

[51] Int. Cl.$^5$ .............................................. A61B 5/00
[52] U.S. Cl. .............................. 128/736; 364/413.03
[58] Field of Search ............. 128/736, 639, 640, 644, 128/798, 915, 916; 374/110, 112, 113, 208; 364/413.03, 413.04, 413.02, 557

[56] References Cited

U.S. PATENT DOCUMENTS

| Re. 32,000 | 10/1985 | Sagi . | |
| 3,830,224 | 8/1974 | Vanzetti et al. | 128/736 |
| 3,847,139 | 12/1974 | Flam | 128/736 |
| 4,031,365 | 6/1977 | Raggiotti et al. . | |
| 4,055,166 | 10/1977 | Simpson et al. . | |
| 4,186,748 | 2/1980 | Schlager . | |
| 4,275,741 | 6/1981 | Edrich | 128/653 |
| 4,465,077 | 8/1984 | Schneider | 128/738 |
| 4,524,778 | 6/1985 | Brown, Jr. et al. | 128/736 |
| 4,593,698 | 6/1986 | Athans | 128/644 |
| 4,682,605 | 7/1987 | Hoffman | 128/736 |
| 4,774,961 | 10/1988 | Carr | 128/736 |
| 4,798,209 | 1/1989 | Klingenbeck et al. | 128/653 |
| 4,849,885 | 7/1989 | Stillwagon et al. | 364/413.1 |
| 4,872,122 | 10/1989 | Altschuler et al. | 364/554 |
| 5,042,481 | 8/1991 | Suzuki et al. | 128/639 |
| 5,054,496 | 10/1991 | Wen et al. | 128/696 |
| 5,092,343 | 3/1992 | Spitzer et al. | 128/733 |
| 5,095,916 | 3/1992 | Smits | 128/784 |

OTHER PUBLICATIONS

"Nerves of Silicon" by T. A. Heppedheimer, Discover, Feb. 1988, pp. 70-79.
"An Introduction to Computing With Neural Nets" by Richard P. Lippmann, IEEE ASSP Magazine, Apr., 1987, pp. 4-22.

Primary Examiner—Stephen C. Pellegrino
Assistant Examiner—Guy V. Tucker
Attorney, Agent, or Firm—R. William Graham

[57] ABSTRACT

The present invention relates to a device for detecting and monitoring physiological conditions in mammalian tissue, and method for using the same. The device includes sensors for sensing physiological conditions and generating signals in response thereto and processor operatively associated with the sensors for receiving and manipulating the signals to produce a generalization indicative of normal and abnormal physiological condition of mammalian tissue. The processor is characterized to include a neural network having a predetermined solution spaced memory, the solution space memory including regions indicative of two (2) or more physiological conditions, wherein the generalization is characterized by the signals projected into the regions.

1 Claim, 2 Drawing Sheets

DEVICE FOR DETECTING CANCEROUS AND PRECANCEROUS CONDITIONS IN A BREAST

BACKGROUND OF THE INVENTION

This invention is directed to a device which indicates abnormal physiological conditions, and more particularly to, but not by way of limitation, a device for monitoring mammalian temperature for use in determining cancerous conditions.

It is known that areas of mammalian tissue adjacent to carcinomas exhibit increased temperature from that exhibited contemporaneously by non-adjacent, non-cancerous areas. The temperature of the cancer-affected areas can fluctuate several degrees Centigrade from normal tissue; these differences having been demonstrated while monitoring such areas for a 24-hour period (one circadian cycle).

It had been thought that an abnormal temperature pattern associated with a tumor is a product of accelerated metabolism. Evidence now suggests that local metabolic heat generation may be a second order effect since the majority of thermal signals are related to the function of increased regional blood flow caused by local angiogenesis. A slight overall increase in the temperature of the surrounding tissue, for instance in localized areas of a woman's breast, can occur and is usually related to the vascular convection of heat that occurs as a result of capillary dilatation and the secondary increase in blood flow coupled with the higher temperature of the blood derived from the vascular bed and the possible vasodilator effect of catabolic products of tumor metabolism. These vascular manifestations of heat production are of prime importance in the detection of subclinical or minimal cancers.

A prior device used for detecting cancer is a brassiere which includes a plurality of temperature sensors, an analog multiplexer circuit, a control circuit, a sample and hold circuit, an analog/digital converter, a buffer register, a storage register, a clock and a data logger. The device allows for the storage of temperature readings in a digital form. This digital data may be uploaded to the data logger which converts the digital signals to decimal form so that the temperature differences may be read and analyzed by a supervising physician.

Several problems exist with the brassiere device. The brassieres must be capable of fitting a full range of breast sizes since tissue contact is essential to device performance. Also, this system would be expensive requiring individual brassieres to be prepared for each user since it is unlikely that an individual would wear a brassiere which was previously worn by another person for extended periods of time due to the nature of the device. Thus, a disposable brassiere would be desired.

Furthermore, the temperature sensors of the brassiere device are affixed on its inner surface. Ideally, all sensors are in contact with the skin when the brassiere is positioned about the breast. Realistically, however, in the normal course of wear, the sensors will frequently not be in contact with the skin. Lack of contact causes the sensors to produce false skin temperature readings. It is also noted that such device does not disclose a need or means for calibrating the sensors. Any diagnosis based on uncalibrated sensor readings could be faulty.

Other devices use a passive thermographic analytical apparatus which provides a direct readout of the results through analysis of a thermographic radiation pattern of the human body. Such devices include a matrix of infrared energy sensors and reflectors which are mounted in a closed, spaced array to produce a pattern of temperature measurement of the aligned areas of the body. The sensors simultaneously or sequentially read a thermographic pattern and develop analog signals which are converted into the appropriate digital form and are stored in a memory. The digital signals are then analyzed by a central processing unit (cpu) in accordance with a particular spatial pattern recognition software program. The program includes an algorithm having a number of parameters used in comparing differences in temperatures throughout the breasts to give a probability of breast normality or abnormality.

Unfortunately, such devices are unable to detect small tumors on the order of less than 0.5 cm. This seems to be due to the resolution and sensitivity capabilities of the thermographic sensors. Another problem with such devices is that the cpu will give inaccurate results if internal failure occurs at any point in the computer's probability program. Faulty readings from the thermographic pattern cause the software program to generate inaccurate results.

Of even greater concern, such thermographic devices do not take into account the chaotic fluctuation of normal body temperatures over time and between locations on the body. The temperatures between the left and right breasts may vary as much as 7 degrees Centigrade during any one circadian cycle. Since the patient is required to remain i front of the scanning apparatus of the thermographic device for only a short period of time in order to take a thermographic picture, that picture only represents one moment in time and is not representative of the actual condition of the breast over a long period of time. An analysis based on such thermographic results could be totally inaccurate.

One common and widely used technique for determining existence of breast cancer is mammography. This radiological technique passes ionizing radiation through the breast, which is per se invasive, to produce a radiographic which should report tumors as darkened areas. This method of detecting breast cancer is limited by the age and condition of the tissue examined. If the tissue is dense, as is characteristic of breast tissue in younger women, the image produced is more uniform in color causing detection of tumors to be more difficult. Further disadvantages of the previous systems are that they are relatively expensive and cumbersome compared to the present invention.

SUMMARY OF THE INVENTION

It is an object of the present invention to provide a non-invasive device which can constantly sense physiological conditions in a mammalian body over a circadian period and is adapted to be worn on the mammalian body while performing daily activities.

Another object of the present invention is to provide a breast cancer detecting device which is capable of accurately sensing physiological conditions in mammalian tissue.

An object of the present invention is to provide means and method for determining the normality or abnormality of areas of the breast highly susceptible to cancer development.

It is yet another object of the present invention to provide a device for detecting in situ cancerous tumors and precancerous lesions. It is a particular object of the present invention to provide a device capable of detecting breast cancer and its general location with a relatively high degree of accuracy.

Still another object of the present invention is to provide a relatively inexpensive and reusable device for monitoring and analyzing physiological conditions.

The present invention is directed to a device for detecting physiological conditions in a mammalian body. The device comprises means for sensing physiological conditions and generating signals in response thereto and means operatively associated with the sensing means for receiving and manipulating the signals to produce a generalization indicative of normal and abnormal physiological condition of the subject.

The receiving and manipulating means includes processing means having non-algorithmic logic which utilizes prior pathological data in correspondence with the sensed signals to manipulate the signals to produce the generalization.

In another embodiment, the receiving and manipulating means is further characterized to include a neural network having predetermined solution space memory, the solution space memory including regions indicative of two or more physiological conditions, wherein the generalization is characterized by the signals projected into regions.

The device further includes means operatively connecting the sensing means and the receiving and manipulating means; the connecting means includes means for receiving and storing the signals from the sensing means, means for controlling transmission of the signals from the sensing means to the storing means, and means for calibrating the sensing means.

The device further includes a template shaped to orient with respect to and to conform to a mammalian breast for spatially positioning the sensing means in accordance with areas of the breast predetermined highly susceptible to cancer development.

Also provided is a method for determining abnormal and normal physiological conditions in mammalian tissue which comprises the steps of (a) positioning physiological condition sensors upon the tissue and generating signals in response thereto and (b) manipulating the signals to produce a generalization about the signals indicative of abnormal and normal physiological conditions. The method is further characterized by including in step (a) placing a template over the breast prior to positioning of the sensors so that the sensors can be oriented and positioned with respect to areas of the tissue highly susceptible to cancer development.

The present invention is more particularly described in the drawings and specification which follow.

DETAILED DESCRIPTION OF THE PREFERRED EMBODIMENT

Figure 1:
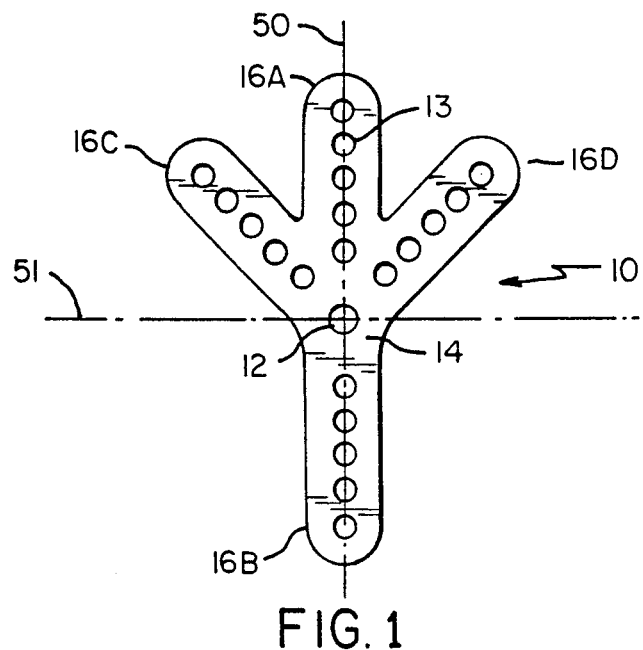
FIG. 1 shows the template of the present invention.

FIG. 1 illustrates template 10. The template 10 is made of a material capable of conforming to a mammalian breast. When the template is properly oriented, the template 10 has a plurality of openings 12 and 13 which are spatially positioned in accordance with areas of the breast pathologically determined to be highly susceptible to cancer development. As shown in FIG. 1, the template 10 has a center portion 14 and four arms 16a–d extending radially outwardly from central portion 14. The template 10 is of a sufficient size to accommodate numerous breast sizes. Central portion 14 has the opening 12 centrally defined therein which is placed over the breast nipple to position the template. Each arm 16a–d has a sufficient quantity of the openings 13 to accommodate differing breast sizes such that at least one opening per arm can be placed over a breast area desired to be sensed.

Areas of the breast to be sensed, for example those where cancer development is most likely to occur, can be marked by orienting the template 10 on a breast as shown in FIG. 1. Arms 16a and 16b extend along the vertical midline 50 of the breast with arm 16a above and arm 16b below the horizontal midline 51 of the breast. Arms 16c and 16d extend diagonally to bisect the upper outer quadrant and upper inner quadrant of the breast, respectively. On the patient's other breast, the position of arms 16c and 16d are reversed which allows for symmetrical markings of the breasts, important in obtaining an accurate diagnosis.

Figure 2:
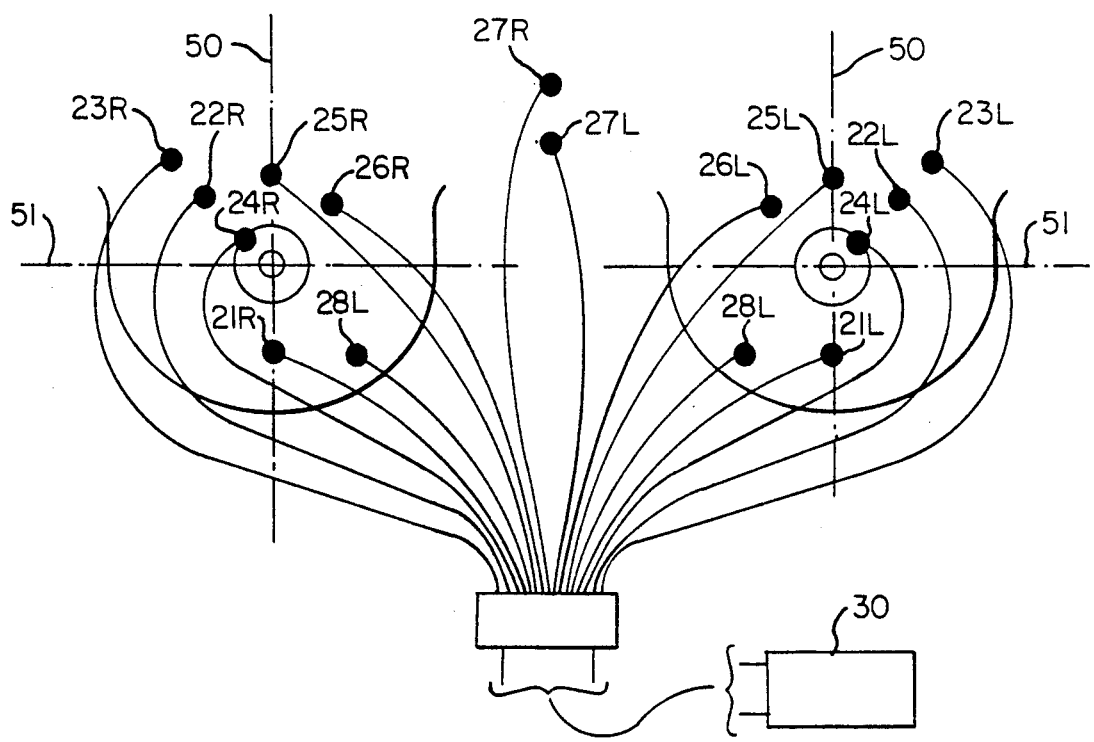
FIG. 2 shows the sensors and harness block of the present invention.

Once location of desired sensor placement has been determined, the sensors (in the preferred embodiment the sensors are thermistors) are affixed to the breast tissue. FIG. 2 illustrates thermistors 21L–28L and 21R–28R positioned on the breasts and attached to harness block 30 according to the invention. Thermistors 21L–28L and 21R–28R are positioned over the marked areas of the right and left breasts which have been determined by use of template 10. Specifically, thermistors 21L–28L and 21R–28R are placed on the breasts as follows: 21L and 21R below the nipple; 22L and 22R in the upper outer quadrant; 23L and 23R in the upper outer quadrant toward the axilla; 24L and 24R on the upper areola; 25L and 25R on vertical midline 50 above horizontal midline 51; 26L and 26R in the upper inner quadrant; 27L in an ambient temperature zone; 27R on the sternum; 28L and 28R on other areas of concern and at contralateral positions. Each pair of the thermistors (e.g., 21L/21R, 22L/22R, etc.) is preferably marked to allow for easy identification of each thermistor pair as well as each thermistor. For example, each thermistor pair is color coded and tabbed with a number and letter. Each thermistor and its signals are consequently identified with a specific position on the breast. This consistency simplifies subsequent processing and improves accuracy of the signals in terms of individual signal correlation with calibration data and selection of specific signal sources for manipulation in developing the generalization of physiological condition. This also simplifies correlation of results with specific sensor positions on the breast to arrive at a more specific determination of the location of abnormal physiological condition. While the number of thermistors and positioning are specifically set forth, it is conceived that accuracy increases as the number of thermistors increases.

Each of the thermistors 21L–28L and 21R–28R is made of an electrically conductive material (e.g. nickel-manganese oxide). Each thermistor produces a resistance which varies with the temperature measured. An important feature of the present invention resides int he calibration system of the thermistors. In the instant invention, the Steinhart and Hart equation, an empirical expression, has been determined to be a suitably desirable signal transform algorithm for the resistance-temperature relationship. It is usually found explicit in T, with:

$$1/T = a + b(Ln\ R) + C(Ln\ R)3$$

and in which T is the Kelvin temperature, Ln R is the Logarithm of R to the base e and a, b and c are coefficients derived from measurement.

Normalization coefficients a, b and c are found by making measurements of R at three Temperatures (20 degrees, 30 degrees, and 40 degrees C) and solving simultaneously:

$$1/T = a + b(Ln\ R1) + C(Ln\ R1)3$$

$$1/T2 = a + b(Ln\ R2) + C(Ln\ R2)3$$

$$1/T3 = a + b(Ln\ R3) + C(Ln\ R3)3.$$

Over a temperature range of 20 degrees to 40 degrees Centigrade (C), this algorithm produces an accurate fit. Because each thermistor has slightly different physical and chemical properties, the resistance of each thermistor is measured at 20 degrees C, 30 degrees C, and 40 degrees C in a stirred nonconductive fluid bath, (e.g. BLANDOL TM available from Sealand Chemical, Silicon oil or FLURINERT 40 TM available from Sealand Chemical, the fluid temperature measured by a NIST standard thermometer, and the specific normalization coefficients for each thermistor determined by inserting the resistances of each thermistor at each temperature into and simultaneously solving the foregoing equations.

Figure 3:
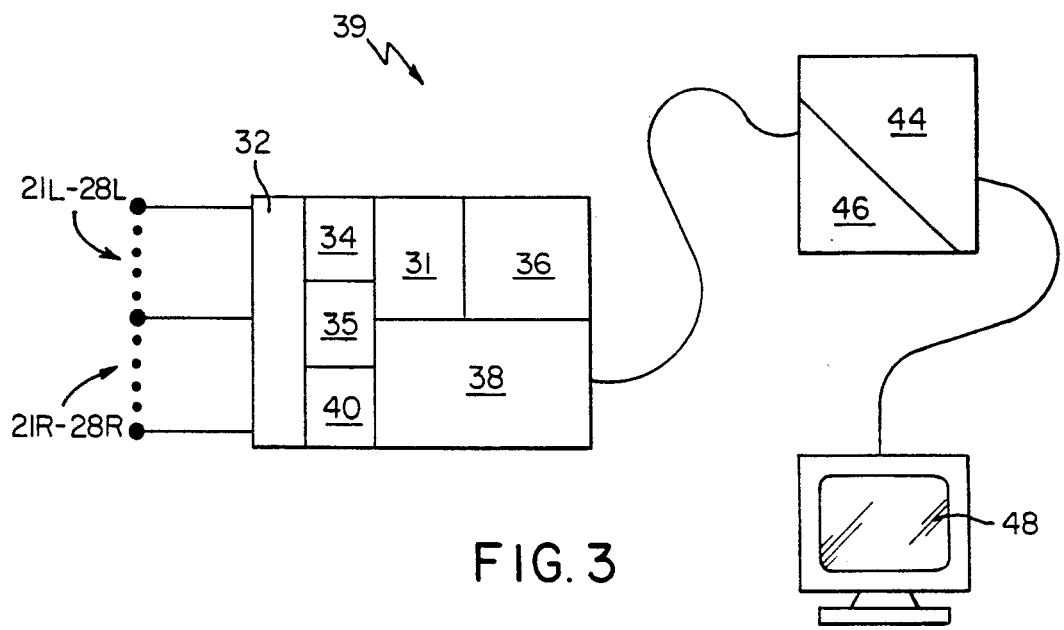
FIG. 3 is a schematic drawing of the present invention.

Referring to FIG. 3, these coefficients are referred to as calibration data which are stored in memory 31 (read only memory, for example) of harness 30 and identified as relating to a specific thermistor. An important aspect of the present invention is that the calibration data is stored in harness block 30. In the field of use, many harness blocks will exist. Accessing each thermistor's calibration data contemporaneously with its respective stored signals from the harness block will remove the potential for processing errors occurring from mismatching calibration data and thermistors.

Each of thermistors 21L-28L and 21R-28R is connected to an analog multiplexer 32 which allows for simultaneous transmission of signals from the thermistors 21L-28L and 21R-28R to analog/digital (A/D) converter 34. Each signal is then amplified by amplifier 35 and applied to A/D converter 34 which converts each analog signal into a suitable multiple bit binary number or word suitable for processing.

Within harness 30, an oscillator type system clock 40 supplies pulses to CPU 38. Upon receiving a predetermined number of pulses, CPU 38 initiates multiplexer 32 to poll thermistors 21L-28L and 21R-28R by gating signals from each thermistor 21L-28L, 21R-28R. CPU 38 controls the transmission and storing of the signals in random access memory 36. Multiplexer 32, A/D converter 34, memory 36, CPU 38, clock 40, and amplifier 42 are of any suitable construction as is known in the art.

FIG. 3 shows fully configured device 39 which includes a CPU 44 operatively associated with neural network 46 and CPU 38. CPU 44 is capable of uploading data from memory 31 and 36 and channeling the data through neural network 46. The CPU 44 can be a commercially available microprocessor which uses the software system described herein below. Alternatively, a commercially available microprocessor can be integrated with a commercially available neurocomputer accelerator board, such as the one available from Science Applications International Corp. (SAIC).

Neural network 46 utilizes parallel processing which allows quantities of information, or data, to be analyzed more quickly and in a different fashion than is permitted in serial processing.

Generally speaking, neural network paradigms make no assumptions about the data and feature segmentation is automatically performed. The network itself selects, through a non-algorithmic process, features of the input data on which it focuses at any point during data processing and manipulation. Where the desire is to receive output results related to normal or abnormal physiological condition, the features are weighted based on pathological evidence and other empirical data introduced into the neural network through what is referred to as a training process.

Generally speaking, the neural network training process entails the creation of a solution space memory. Solution space memory as used herein refers to multidimensional space created internal to the neural network containing regions associated with pathological determinations of normal physiological condition and other regions associated with abnormal physiological conditions. The training process further entails iteratively entering empirical data and pathological evidence and modulating the neural network based upon its output. This iterative training accomplishes several purposes, first refining the definition of the regions associated with each condition in the solution space memory, and second causing the neural network to determine the non-algorithmic process by which it projects new data signals into the solution space. Following training, the neural network, will manipulate and project input signals into the solution space memory and the resulting intersection of those signals with one or more solution space regions produces a generalization about the signal indicative of abnormal or normal physiological condition. Provided that sufficient pathological and other empirical data is available to train the neural network, its manipulation methodology, based on parallel processing, produces results consistent with invasive pathological determinations made through mammography and biopsy techniques.

A display 48 is connected to the CPU 44 such that the display 48 provides access to the results generated by the neural network 46 and CPU 44 based upon the input data received thereby.

Figure 4:
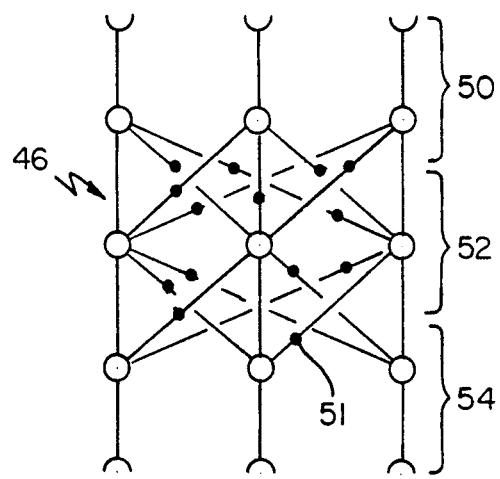
FIG. 4 is a general diagram of the neural network of the present invention.

As shown in FIG. 4, the neural network 46 includes at least one layer of trained neuron-like units, and preferably at least three layers. The neural network 46 includes input layer 50, hidden layer 52, and output layer 54. Each of the input, hidden, and output layers include a plurality of trained neuron-like units.

The neuron-like units of the input layer include a receiving channel for receiving a sensed signal, wherein the receiving channel includes a predetermined modulator for modulating the signal. The neuron-like units of the hidden layer are individually receptively connected to each of the units of the input layer. Each connection 51 includes a predetermined modulator for modulating each connection between the input layer and the hidden layer.

The neuron-like units of the output layer are individually receptively connected to each of the units of the hidden layer. Each connection 51 includes a predetermined modulator for modulating each connection between the hidden layer and the output layer. Each unit of said output layer includes an outgoing channel for transmitting the modulated signal.

Figure 5:
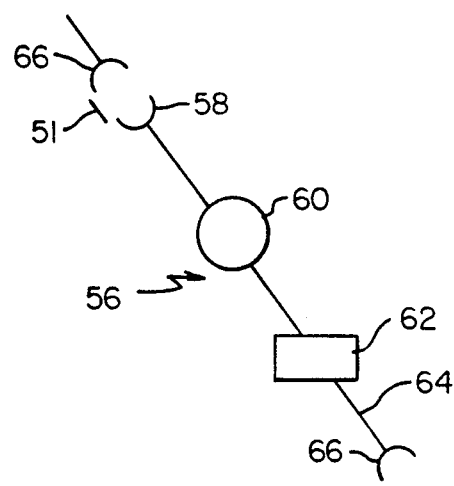
FIG. 5 represents a neuron-like unit of the present invention.

Referring to FIG. 5, each trained neuron-like unit 56 includes a dendrite-like unit 58, and preferably several, for receiving analog incoming signals. Each dendrite-like unit 58 includes a particular modulator 60 which modulates the amount of weight which is to be given to the characteristic sensed by modulating the incoming signal and subsequently transmitting a modified signal. For software, the dendrite-like unit 58 includes an input variable $X_A$ and a weight value $W_A$ wherein the connection strength is modified by multiplying the variables together. For hardware, the dendrite-like unit 58 can be a wire, optical or electrical transducer having a chemically, optically or electrically modified resistor therein.

Each neuron-like unit 56 includes soma-like unit 62 which has a threshold barrier defined therein for the particular characteristic sensed. When the soma-like unit 62 receives the modified signal, this signal must overcome the threshold barrier whereupon a resulting signal is formed. For software, the soma-like unit 62 is represented by the sum $S = \Sigma_A X_A W_A - \beta$, where $\beta$ is the threshold barrier. This sum is employed in a Nonlinear Transfer Function (NTF) as defined below. For hardware, the soma-like unit 62 includes a wire having a resistor; the wires terminating in a common point which feeds into an operational amplifier having a nonlinear part which can be a semiconductor, diode, or transistor.

The neuron-like unit 56 includes an axon-like unit 64 through which the output signal travels, and also includes at least one bouton-like unit 66, and preferably several, which receive the output signal form axon-like unit 64. Bouton/dendrite linkages form the connection 51 from the input layer to the hidden layer and from the hidden layer to the output layer. For software, the axon-like unit 64 is a variable which is set equal to the value obtained through the NTF and the bouton-like unit 66 is a function which assigns such value to a dendrite-like unit of the adjacent layer. For hardware, the axon-like unit 64 and bouton-like unit 66 can be a wire, an optical or electrical transmitter.

The modulators of the input layer modulate the amount of weight to be given various physiological characteristics such as, but not necessarily limited to, temperature, temperature fluctuation, area of the body sensed, physiological period of month (menstrual), and pre or perimenopausal status.

For example, if a patient's tissue temperature is higher than, lower than, or in accordance with what has been predetermined as normal, the soma-like unit would account for this in its output signal and this bears directly on the neural network's decision to indicate whether a normal or an abnormal condition exists.

The modulators of the output layer modulate the amount of weight to be given for indicating normal physiological conditions or abnormal physiological conditions. It is also possible, however, to assign weighting unit values to output neuron-like units which represent a probability of normal or abnormal conditions, e.g. 90 percent likely to be abnormal conditions. It is not exactly understood what weight is to be given to characteristics which are modified by the modulators of the hidden layer, as these modulators are derived through a training process defined below.

The training process is the initial process which the neural network must undergo in order to obtain and assign appropriate weight values for each modulator. Initially, the modulators and the threshold barrier are assigned small random non-zero values. The modulators can be assigned the same value bu the neural network's learning rate is best maximized if random values are chosen. Pathological and other empirical data taken from control group subjects over one circadian period of forty-eight hours at predetermined intervals is input in parallel into the dendrite-like units of the input layer and the output observed.

The NTF employs S in the following equation to arrive at the output:

$$NTF = \frac{1}{[1 + e^{-s}]}$$

For example, in order to determine the weight to be given to each modulator for the particular physiological variable, the NTF is employed as follows:

If the NTF approaches 1, the soma-like unit produces an output signal indicating an abnormal condition. If the NTF approaches 0, the soma-like unit produces an output signal indicating a normal condition. If the output signal clearly conflicts with the known conditions, pathologically determined, an error occurs. The weight values of each modulator are then adjusted using the following formulas so that the input data produces the desired empirical output signal.

For the output layer:

$$W^*_{ko1} = W_{ko1} + GE_k Z_{kos}$$

$W^*_{ko1}$ = new weight value for neuron-like unit k of the output layer.

$W_{ko1}$ = actual weight value obtained for neuron-like unit k of the output layer.

G = gain factor (usually less than 1.0)

$Z_{kos}$ = actual output signal of neuron-like unit k of output layer.

$D_{kos}$ = desired output signal of neuron-like unit k of output layer.

$E_k = Z_{kos}(1 - Z_{kos})(D_{kos} - Z_{kos})$, (this is an error term corresponding to neuron-like unit k of output layer).

For the hidden layer:

$W^*_{jh1} = W_{jh1} + GE_j Y_{jos}$ $W^*_{jh1}$ = new weight value for neuron-like unit j of the hidden layer.

$W_{jh1}$ = actual weight value obtained for neuron-like unit j of the hidden layer.

G = gain factor (generally less than 1)

$Y_{jos}$ = actual output signal of neuron-like unit j of hidden layer.

$E_1 = Y_{jos}(1 - Y_{jos}) \Sigma_k E_k W_{ko1}$, (this is an error term corresponding to neuron-like unit j of hidden layer over all k units).

For the input layer:

$W^*_{ii1} = W_{ii1} + GE_i X_{ios}$ $W^*_{ii1}$ = new weight value for neuron-like unit i of input layer.

$W_{ii1}$ = actual weight value obtained for neuron-like unit i of input layer.

G = gain factor (generally less than 1)

$X_{ios}$ = actual output signal of neuron-like unit i of input layer.

$E_i = X_{ios}(1-X_{ios})\Sigma_j E_1 W_{jh1}$, (this is an error term corresponding to neuron-like unit i of input layer over all j units).

The process is iteratively repeated by entering further empirical data into the neural network and observing the output signal. If the output is in error with what the known output should be, the weights are adjusted in the manner described above. Utilizing input data known to correspond to actual physiological conditions pathologically determined, this process continues until the output is substantially consistent with such pathologically determined physiological conditions. The weights are then fixed.

Upon fixing the weights of the modulators, a solution space memory with regions indicative of normal and abnormal physiological conditions is established in the neural network. The neural network is at this stage considered trained and can make generalizations about input data by projecting input data into the solution space memory and determining which regions the input data intersects. The generalization is improved by comparing input data taken repetitively at intervals over a period of time, in the present invention taking temperature readings every five minutes over one circadian cycle, although it is recognized that a different interval may still provide reliable results. The generalization relates not only to the breast as a whole but also is capable of identifying abnormal physiological conditions with a specific quadrant of the breast.

While the preferred embodiment has employed the neural network to carry out the invention, it is conceived that other means, such as a statistical program, might be used instead of or in conjunction with the neural network. It is conceived that many variations, modifications and derivatives of the present invention are possible and the preferred embodiment set forth above is not meant to be limiting of the full scope of the invention. It is comprehended by the inventors that the device, and in particular the neural network, may be used to determine heart disease, circulatory clogging, characterization of tissue type and other physiological conditions which exhibit chaotic behavior.

The following example is presented for the purpose of illustrating the present invention, but is not intended to be limiting in the nature and scope of the present invention.

Method 138 subjects were recruited from the population at a surgical oncology clinic who had been scheduled for open-breast biopsies as a result of physical exam and mammography. Each subject wore the harness block/sensors of the present invention for a period of forty-eight hours wherein data readings were taken every five minutes.

The data were analyzed using the neural network described above which was trained using fifty-seven exemplar cases. The following results were obtained.

| | |
|---|---|
| Total biopsies: | 138 |
| Positive for cancer: | 23 |
| Cancer found by mammogram: | 19 |
| Cancer found by present invention: | 21 |
| Palpable cancers: | 17 |
| Needle localization: | 6 |

Three of the cancers detected by the present invention but not by mammography had sizes of 0.5, 0.7, and 2.0 cm in subjects aged 36, 38 and 44 respectively. In addition, the present invention indicated an additional 21 of the subjects as high risk to cancer development.

What is claimed is:

1. A device for detecting cancerous and precancerous conditions in a mammalian breast, comprising:

non-invasive means for sensing temperature in the breast and generating a signal in response thereto, wherein said sensing means includes a plurality of temperature sensors removably affixable to the breast and capable of sensing over at least one circadian period; and means for receiving and manipulating said signal and for producing an output signal indicative of cancerous and precancerous conditions in the breast, said receiving and manipulating means including neural network means for producing a generalization about said signal, wherein said generalization is used in forming said output signal; and a relatively flexible template shaped to orient with respect to and to conform to said mammalian breast, wherein said template includes a central portion, and a plurality of arms extending radially outward from and at predetermined angles with respect to a vertical midline and a horizontal midline which extend through said central portion, said arms further defining a pattern wherein a greater number of said arms are above said horizontal midline to exhibit an orienting characteristic, and wherein said central portion has an opening and each said arm has a plurality of openings to accommodate for varying breast sizes so that markings can be made on areas of said breast to allow for spatially positioning said temperature sensors in accordance with said marked areas of the breast.

* * * * *